(12) United States Patent
Smith et al.

(10) Patent No.: US 7,019,188 B2
(45) Date of Patent: Mar. 28, 2006

(54) USE OF IONIC LIQUIDS TO SEPARATE OLEFINS, DIOLEFINS AND AROMATICS

(75) Inventors: Ronald Scott Smith, Calgary (CA); Patricio S Herrera, Calgary (CA); Sean Reynolds, Calgary (CA)

(73) Assignee: Nova Chemicals (International) S.A., (CH)

( * ) Notice: Subject to any disclaimer, the term of this patent is extended or adjusted under 35 U.S.C. 154(b) by 622 days.

(21) Appl. No.: 10/172,447

(22) Filed: Jun. 14, 2002

(65) Prior Publication Data

US 2004/0225172 A1 Nov. 11, 2004

(51) Int. Cl.
*C07C 7/08* (2006.01)
*C07C 7/10* (2006.01)
*C07C 7/152* (2006.01)

(52) U.S. Cl. ............... 585/809; 585/810; 585/843; 585/845; 585/850; 585/848; 585/860; 585/862; 208/219; 208/223

(58) Field of Classification Search ........... 585/809, 585/810, 843, 845, 850, 848, 860, 862; 208/219, 208/223
See application file for complete search history.

(56) References Cited

U.S. PATENT DOCUMENTS

| 3,441,377 A | 4/1969 | Sawyer et al. ............... 23/204 |
| 3,979,280 A | 9/1976 | Dielacher et al. ......... 208/310 R |
| 4,328,382 A | 5/1982 | Alter et al. ................. 585/844 |
| 5,981,818 A | 11/1999 | Purvis et al. ............... 585/519 |
| 6,339,182 B1 | 1/2002 | Munson et al. ............. 585/809 |
| 6,849,774 B1 * | 2/2005 | Boudreau et al. ........... 585/809 |

FOREIGN PATENT DOCUMENTS

CA 1096779 3/1981

* cited by examiner

*Primary Examiner*—Tam M. Nguyen
(74) *Attorney, Agent, or Firm*—Kenneth H. Johnson

(57) ABSTRACT

The present invention relates to the separation of olefins, diolefins and lower aromatics from mixed streams of hydrocarbons using ionic liquids in the absence of metal compounds. The present invention eliminates the metal complexes conventionally used in such separation and thus reduces the complexity of the process.

12 Claims, No Drawings

USE OF IONIC LIQUIDS TO SEPARATE OLEFINS, DIOLEFINS AND AROMATICS

FIELD OF THE INVENTION

The present invention relates to the separation of alkenes from alkanes using an ionic liquid.

BACKGROUND OF THE INVENTION

In the cracking of feedstocks to produce alkenes the resulting product is typically a mixture of various alkenes, such as ethylene and propylene and various alkanes or paraffins such as ethane, propane, and higher alkanes. With close boiling products such as ethylene and ethane and propylene and propane it is necessary to separate the products using distillation methods. The distillation may be carried out at very low temperatures or may be carried out using higher pressures and corresponding higher temperatures.

It is known to separate olefins from paraffins by forming complexes with metals such as silver or copper. The resulting copper or silver complex is preferentially soluble in a liquid not miscible or soluble in the paraffin, such as water. The streams are separated and then the olefin is released from the complex typically by a temperature or pressure change. The regenerated metal compound is then capable of being reused to complex more olefin. In some cases the metal compound is adsorbed or complexed on the surface of an ion exchange resin or in a membrane separation film and the olefin is separated from the alkane. Representatives of such art include Canadian patent 1,096,779 issued Mar. 3, 1981 to Deutsche Texaco A.G.; U.S. Pat. No. 3,979,280 issued Sep. 7, 1976 and assigned to Deutsche Texaco A.G.; U.S. Pat. No. 4,328,382 issued May 4, 1982 assigned to Erdoelchemie G.m.b.H.; and U.S. Pat. No. 3,441,377, issued Apr. 29, 1969 to Esso Research and Engineering Co.

Most recent in this line of technology is U.S. Pat. No. 6,339,182 B1 issued Jan. 15, 2002 to Munson et al., assigned to Chevron U.S.A. Inc. This patent teaches the absorption of alkenes by metal salts, typically silver or copper salts in ionic liquids. The alkenes are typically initially present as an admixture with paraffins. The alkenes are regenerated by separation from the metal complex by temperature or pressure change or application of an entrainment gas such as an inert gas.

The present invention is distinct over the above art as it does not require the presence of a metal complex. Applicants have discovered that olefins are preferentially soluble in some ionic liquids without the presence a metal (e.g. silver or copper) salt.

The present invention seeks to provide a simple process for the separation of alkenes from other hydrocarbons, particularly alkanes.

SUMMARY OF THE INVENTION

The present invention provides a process for separating one or more members selected from the group consisting of $C_{2-8}$ olefins, $C_{4-8}$ diolefins, and $C_{6-12}$ aromatic hydrocarbons which are unsubstituted or substituted by up to three $C_{1-4}$ alkyl radicals from a mixture comprising at least one of said members and at least one other hydrocarbon comprising contacting said mixture with a nitrogen containing ionic liquid having a melting temperature below 80° C. to preferentially take said one or members into said ionic liquid, separating said ionic liquid from said at least one other hydrocarbon and regenerating said ionic liquid and releasing said at least one member.

DETAILED DESCRIPTION

In accordance with the present invention one or more members selected from the group consisting of $C_{2-8}$ monoolefins, $C_{4-8}$ conjugated diolefins, and $C_{6-8}$ aromatic hydrocarbons may be separated from one or more hydrocarbons, typically paraffins, typically having up to about 20 carbon atoms, preferably $C_{1-18}$ paraffins.

The olefins may be selected from the group consisting of alpha olefins including ethylene, propylene, butene, hexene, and octene, preferably ethylene, butene, hexene, and octene. The olefins may be other than alpha olefins such as 2-methyl-2-butene. Preferably the olefins are hydrocarbyl olefins and do not contain other atoms or functional groups.

The diolefins are typically $C_{4-8}$ diolefins. The diolefins may be conjugated or non-conjugated. Some diolefins include butadiene, including 1,3-butadiene, hexadiene including 1,4-hexadiene and 1,5-hexadiene, and octadiene including 1,7-octadiene. The dienes may be substituted by a $C_{1-4}$ alkyl radical such as isoprene. Preferably the dienes are hydrocarbyl olefins and do not contain other atoms or functional groups.

The $C_{6-12}$ aromatic compounds are also preferably hydrocarbyl compounds. These compounds may be unsubstituted or may be substituted by up to three lower alkyl groups (i.e. $C_{1-4}$ alkyl radicals). This group of compounds includes benzene, toluene, xylene, and naphthalene.

Preferably the compounds being separated from the mixture with other hydrocarbons are mixtures containing olefins, or mono- and diolefins.

The mixtures to be treated in accordance with the present invention may be subject to a number of treatments prior to being contacted with the ionic liquid. Such treatments are well known to those skilled in the art and include for example removal of polar species (e.g. CO, $CO_2$ and water) and hydrogenation such as hydrogenation of acetylenes.

Ionic liquids are organic compounds that are liquid at room temperature. They differ from most salts, in that they have very low melting points. They tend to be liquid over a wide temperature range and have essentially no vapor pressure. Most are air and water stable, and they are used herein to solubilize olefins, diolefins, and/or aromatic hydrocarbons. The properties of the ionic liquids can be tailored by varying the cation and anion. Examples of ionic liquids are described, for example, in J. Chem. Tech. Biotechnol., 68:351–356 (1997); Chem. Ind., 68:249–263 (1996); and J. Phys. Condensed Matter, 5:(supp. 34B):B99–B106 (1993), Chemical and Engineering News, Mar. 30, 1998, 32–37; J. Mater. Chem., 8:2627–2636 (1998), and Chem. Rev., 99:2071–2084 (1999), the contents of which are hereby incorporated by reference.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various counter ions such as Lewis acids or their conjugate bases to form ionic liquids (nitrogen based ionic liquid). Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this tend to increase the melting point of the salt.

Ionic liquids have also been based upon various triarylphosphines, thioethers, and cyclic and non-cyclic quaternary ammonium salts. Counterions which have been used include chloroaluminates, bromoaluminates, gallium chloride, tetrafluoroborate, tetrachloroborate, hexafluorophosphate, nitrate, trifluoromethane sulfonate, methylsulfonate, p-toluenesulfonate, hexa fluoroantimonate, hexa fluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

In accordance with the present invention the organic portion of the ionic liquid is typically a nitrogen containing $C_{5-8}$ hetrocyclic aromatic compound. The hetrocyclic aromatic compound may be unsubstituted or substituted by up to three $C_{1-6}$, preferably $C_{1-4}$ alkyl radicals. The hetrocyclic aromatic compound may be selected from the group comprising pyrrolium, imidazolium, and pyridinium which are unsubstittued or substituted by up to two $C_{1-4}$ alkyl radicals, for example 1-butyl-3-methylimidazolium and 4-methyl-N-butylpyridinium.

Useful counter ions include borate compounds, preferably tetrahaloborates most preferably tetrafluoroborate (the corresponding acid form of Lewis acid would for example be $H^+BF^-_4$). Other counter-ions which may be suitable for use in the present invention are discussed in U.S. Pat. No. 6,339,182.

Some ionic liquids which may be used in accordance with the present invention include 1-butyl-3-methylimidazolium tetrafluoroborate; 1-hexyl-3-methylimidazolium tetrafluoroborate; 4-methyl-N-butylpyridinium tetrafluoroborate; 4-hexyl-N-butylpyridinium tetrafluoroborate; N-butylpyridinium tetrafluoroborate and N-hexylpyridinium tetrafluoroborate. Further or differently substituted homologues of these compounds are within the scope of the present invention. Other ionic liquids would be apparent to those skilled in the art.

The ionic liquid may optionally contain from 0 up to about 15, preferably less than 10% by volume of water.

The above noted olefins, diolefins, and aromatic hydrocarbons can be selectively separated from mixtures containing one or more of such compounds and other hydrocarbons such as paraffins and higher aromatics. The separation involves contacting the mixture containing one or more of the olefins diolefins and lower aromatic hydrocarbons with the ionic liquid. The ionic liquid takes up the olefins, diolefins, and lower aromatic compounds present in the mixture. The ionic liquid is then separated from the mixture (which is free from or has a significantly (e.g. 75%) reduced content of such olefins, diolefins, and lower aromatic compounds. The hydrocarbon stream can be separated from the ionic liquid using conventional means including, for example, decantation, and the like. In the separation of the residual hydrocarbon stream from the ionic liquid care needs to be taken not to subject the ionic liquid to conditions which will cause it to give up the one or more of the olefins, diolefins, and lower aromatic compounds.

The mixture containing one or more of the olefins, diolefins, and lower aromatic hydrocarbons may be contacted with the ionic liquid using well known methods including, co-current, counter-current, or staged in stirred tanks. Countercurrent methods are preferred. The mixture containing one or more olefins, diolefins, or lower aromatic compounds can be in the gas phase or the liquid phase. The ionic liquid will be in the liquid phase. Typically the contact will take place at temperatures less than about 80° C. preferably less than 50° C. desirably less than 35° C., preferably about room temperature (i.e. from 15° C. to 25° C.). The pressure may be low (i.e. up to 1000 psig (6,895 kPa), preferably less than 100 g psi (689.5 kPa). If the contact with the ionic liquid is under pressure the pressure on the ionic liquid should not be reduced until it is desired to release the one or more olefins, diolefins, and lower aromatic compounds from the ionic liquid.

The one or more of the olefins, diolefins, and lower aromatic compounds may then be recovered from the ionic liquids using a number of regeneration techniques. These techniques may include thermal regeneration (increasing the solution temperature to release the olefins, diolefins, and lower aromatic compounds); pressure swing regeneration (reducing the pressure) and combinations thereof. Entrainment gasses, typically inert gasses, preferably nitrogen may also be passed through the ionic liquid to entrain and release the olefins, diolefins, and lower aromatic hydrocarbons from the ionic liquid. Entrainment gasses may be used with either or both of the foregoing techniques to release the olefins, diolefins, and aromatic hydrocarbons from the ionic liquid.

Release of the one or more olefins, diolefins, and lower aromatic compounds may be carried out in a packed tower or flash drum, preferably a packed tower generally by using a combination of increased temperature and/or lower pressure. The temperatures may range from about 100° C. to about 150° C., (although higher temperatures may be required for relatively high molecular weight olefins, diolefins, and aromatic compounds) preferably from about 120° C. to about 140° C., and the pressure may range from vacuum pressures to about 50 psig (345 kPa), preferably from about 10 psig (about 68.9 kPa) to about 30 psig (about 207 kPa). The temperatures should be higher, and the pressures should be lower for higher molecular weight olefins, diolefins, and aromatic compounds. The decomposition temperature of the ionic liquids should not be exceeded.

The packed tower or flash drum may include multi-stage stripping or flashing for increased energy efficiency. In such systems, the ionic solution rich in one or more olefins, diolefins, and/or lower aromatic compounds is flashed and stripped at progressively higher temperatures and/or lower pressures. The design of such systems is well known to those skilled in the art.

Conventional heating means known to those of ordinary skill in the art, including steam and preferably low pressure steam, may be used to release the one or more olefins, diolefins, and lower aromatic compounds from the ionic liquid. One inexpensive heat source in the lower end of the temperature range is quench water. The packed column or flash drum is preferably equipped with a water wash section in the top to prevent entrainment of the desorbed gases.

The ionic liquid solution can then be removed from the bottom of the packed column or tower or flash drum and recycled back to the contact device.

The present invention provides a simple and relatively cheap means to separate ethylene from ethane in an ethane cracker, ethane/propane cracker, or flexi-cracker. Another commercial use is in the separation of propylene from propane, for example, in dehydrogenation facilities. Additionally, the present invention may be applied at the downsteam or back end of a solution or slurry polymerization and in particular a process which may be using dilute monomer as described in U.S. Pat. No. 5,981,818 issued Nov. 9, 1999 to Purvis et al. assigned to Stone & Webster Engineering Corp.

The present invention will now be illustrated by the following non-limiting examples in which unless otherwise indicated weight is in grams and parts is parts by volume.

EXAMPLES

Example 1

$C_3$ Hydrocarbon Absorption by Ionic Liquids

The present example demonstrates the absorption selectivity of 1-butyl-3-methylimidazolium tetrafluoroborate (bmim$^+$ BF$_4^-$) for propylene over propane. The testing apparatus consists of two sample cylinders (one 1000 cc cylinder and one 150 cc cylinder) connected by ⅛-inch tubing with valves allowing for isolation of each cylinder. A digital pressure gauge indicates the larger cylinder pressure and the pressure of the system when the cylinders are not isolated.

To measure absorption, 50 mL of bmim$^+$ BF$_4^-$ absorbent was loaded into the smaller cylinder and the larger cylinder was pressurized with the hydrocarbon gas. The amount of gas absorbed by the sample of bmim$^+$BF$_4^-$ is proportional to the pressure drop that occurs when the sample is exposed to the test gas, and can be calculated knowing the internal volume of the closed system.

The sample was then exposed to the gas in the large 1000 cc cylinder as the valve separating the cylinders was opened. The initial pressure drop was recorded. The sample was stirred via magnetic stirrer. When the system came to equilibrium (no pressure changed for over 1 hour) the final absorption pressure was recorded and the cylinders were once again separated. This procedure could be repeated for different absorption pressures. Experiments were conducted at ambient temperature.

Between experimental runs, the absorbent was degassed by bubbling a nitrogen entrainment gas through the absorbent for 2 to 3 hours.

Absorption experiments conducted for propylene and propane at different pressures yielded absorption profiles. Table 1 summarizes the findings.

TABLE 1

Gas Absorption by bmim$^+$ BF$_4^-$ Ionic Liquid

| Pressure (psig) | Propane (mol C$_3$H$_8$/L absorbent) | Propylene (mol C$_3$H$_6$/L absorbent) | C$_3$H$_6$:C$_3$H$_8$ Selectivity |
|---|---|---|---|
| 50.0 | 0.011 | 0.039 | 3.55 |
| 72.6 | 0.012 | 0.119 | 9.92 |

Example 2

$C_3$ Hydrocarbon Absorption by Ionic Liquids Containing Water

The procedure described in Example 1 was performed with bmim$^+$ BF$_4^-$ containing 10 (vol)% water and demonstrates an enhancement of absorption selectivity of the water-containing ionic liquid bmim$^+$ BF$_4^-$ for propylene over propane. Table 2 summarizes the findings.

TABLE 2

Gas Absorption by bmim$^+$ BF$_4^-$ Ionic Liquid Containing Water

| Pressure (psig) | Propane (mol C$_3$H$_8$/L absorbent) | Propylene (mol C$_3$H$_6$/L absorbent) | C$_3$H$_6$:C$_3$H$_8$ Selectivity |
|---|---|---|---|
| 50.9 | 0.014 | 0.161 | 11.5 |
| 65.5 | 0.049 | 0.211 | 4.31 |

Example 3

$C_5$ Hydrocarbon Solubility by Ionic Liquids

The present example investigated the solubility of paraffin, olefin, and diolefin $C_5$ hydrocarbons, isopentane, 2-methyl-2-butene, and isoprene respectively, in 1-butyl-3-methylimidazolium tetrafluoroborate (bmim$^+$ BF$_4^-$) and demonstrates the corresponding selectivity for olefinic and diolefinic C5s over corresponding paraffin. The testing apparatus consisted of a flat-bottomed florence flask with a graduated neck. The flask was charged with 75 mL of bmim$^+$ BF$_4^-$, the level being recorded. A known quantity of C5 hydrocarbon was then added to the flask and the flask was sealed. The overall liquid level and the location of the liquid-liquid interfacial meniscus were recorded. The mixture was then agitated to contact the two liquids and the two phases were allowed to separate. The locations of all meniscuses were then recorded. Agitation and phase separation was then repeated until the liquid levels remained unchanged. The volume change of the hydrocarbon phase corresponds to the quantity of hydrocarbon dissolved in the ionic liquid. The testing was conducted at ambient temperature. The results are summarized in Table 3.

TABLE 3

C5 Solubility in bmim$^+$ BF$_4^-$ Ionic Liquid

| Hydrocarbon | Solubility (mol C5/L ionic liquid) | Selectivity over Isopentane |
|---|---|---|
| Isopentane | 0.034 | — |
| 2-Methyl-2-Butene | 0.360 | 10.6 |
| Isoprene | 0.611 | 18.0 |

Example 4

$C_5$ Hydrocarbon Solubility by Ionic Liquids

The procedure described in Example 3 was performed instead with ethylcyclohexane, ethylbenzene, and styrene. The ionic liquids used were 1-butyl-3-methylimidazolium tetrafluoroborate and 4-methyl-N-butylpyridinium tetrafluoroborate (mbpy$^+$ BF$_4^-$). Table 4 summarizes the findings.

TABLE 4

Cyclo-C8 Solubility in Ionic Liquids

| Hydrocarbon | Solubility in bmim$^+$ BF$_4^-$ (mol C8/L ionic liquid) | Solubility in mbpy$^+$ BF$_4^-$ (mol C8/L ionic liquid) |
|---|---|---|
| Ethylcyclohexane | 0.000 | 0.000 |
| Ethylbenzene | 0.530 | 0.551 |
| Styrene | 3.349 | — |

What is claimed is:

1. A process for separating one or more members selected from the group consisting of $C_{2-8}$ mono-olefins, $C_{4-8}$ diolefins, and $C_{6-12}$ aromatic hydrocarbons which are unsubstituted or substituted by up to three $C_{1-4}$ alkyl radicals from a mixture comprising at least one of said members and at least one other hydrocarbon comprising contacting said mixture with an ionic liquid containing a $C_{5-8}$ nitrogen containing aromatic compound which is unsubstituted or substituted by up to three $C_{1-6}$ alkyl radicals, said ionic liquid having a melting temperature below 80° C., in the absence of a metal complex to preferentially take said one or more members into said ionic liquid, separating said ionic liquid from said at least one other hydrocarbon and regenerating said ionic liquid and releasing said at least one member.

2. The process according to claim 1, wherein said ionic liquid is a tetrafluoroborate ionic liquid.

3. The process according to claim 2, wherein said ionic liquid is selected from the group consisting of imidazolium and pyridinium ionic liquids which are unsubstituted or substituted by up to two $C_{1-4}$ alkyl radicals.

4. The process according to claim 3, wherein said ionic liquid is selected from the group consisting of 1-butyl-3-methylimidazolium tetrafluoroborate and 4-methyl-N-butylpyridinium tetrafluoroborate.

5. The process according to claim 4, wherein said mixture is in the gas or liquid state.

6. The process according to claim 5, wherein said regeneration of ionic liquid and said releasing of at least one member is effected using one or more treatments selected from the group consisting of increasing temperature, decreasing pressure, and passing an entraining gas through said ionic liquid.

7. The process according to claim 6, wherein said mixture and said ionic liquid are contacted in a counter-current flow.

8. The process according to claim 6, wherein said mixture and said ionic liquid are contacted in co-current flow.

9. The process according to claim 6, wherein said mixture and said ionic liquid are contacted in a continuous stirred tank reactor.

10. The process according to claim 1, wherein the ionic liquid optionally contains from 0 to 15 volume % of water.

11. The process according to claim 3, wherein the ionic liquid optionally contains from 0 to 15 volume % of water.

12. The process according to claim 4, wherein the ionic liquid optionally contains from 0 to 15 volume % of water.

* * * * *